United States Patent [19]

Doron

[11] 4,311,711
[45] Jan. 19, 1982

[54] BIOCIDAL COMPOSITIONS

[75] Inventor: Arye Doron, Herzlia, Israel

[73] Assignee: Abic Ltd., Ramat-Gan, Israel

[21] Appl. No.: 140,081

[22] Filed: Apr. 18, 1980

Related U.S. Application Data

[63] Continuation of Ser. No. 736,735, Oct. 29, 1976, abandoned.

[30] Foreign Application Priority Data

Nov. 14, 1975 [IL] Israel ........................................ 48475

[51] Int. Cl.$^3$ ............................................ A01N 31/08
[52] U.S. Cl. ..................................... 424/346; 424/347
[58] Field of Search ................................ 424/346, 347

[56] References Cited

U.S. PATENT DOCUMENTS 3,824,190 7/1974 Winicov et al. ..................... 272/106

OTHER PUBLICATIONS

Chemical Abstracts 75:144013c (1971).

*Primary Examiner*—Leonard Schenkman
*Attorney, Agent, or Firm*—Steinberg & Raskin

[57] ABSTRACT

Biocidal compositions are provided comprising a mixture of o-phenylphenol and 2,2'-methylene bis(4-chlorophenol). Said compositions advantageously include a surface active agent which is stable under basic conditions. There are also provided aqueous solutions comprising the above biocidal compositions.

5 Claims, No Drawings

BIOCIDAL COMPOSITIONS

This is a continuation, of application Ser. No. 736,735, filed Oct. 29, 1976, now abandoned.

The present invention relates to biocidal compositions. There are known many biocides, many of them being phenol derivatives. One of said biocidal phenol derivatives is o-phenylphenol. Said compound is quite effective against a broad range of micro-organisms. However, when used against certain other bacteria, in particular against Pseudomonas species which is a wide spread bacteria well known to be an especially biocidal resistant bacteria relatively high levels of said phenol are required.

Another known effective biocidal phenol derivative is 2,2'-methylenebis (4-chlorophenol) (hereinafter called "dichlorophene"). This compound is also effective against a broad range of micro-organisms. However, it is less effective then o-phenylphenol against Pseudomonas species.

U.S. Pat. No. 3,824,190 describes and claims a phenolic-synthetic detergent disinfectant composition comprising a mixture of o-phenylphenol and a phenol selected from the group consisting of 4-chloro-2-cyclopentylphenol, 4-chloro-2-benzylphenol, 4-chloro-2-phenolphenyl, 6-chloro-2-phenylphenol, 4-5-amylphenol, 4-n-amylphenol, 2,4-dichloro-3,5-dimethylphenol, 4-chloro-3,5-dimethylphenol, 5-methyl-2-isopropylphenol, and ortho chloro-p-phenylphenol. It is stated in the specification that said composition is effective, inter alia, against Pseudomonas in hard water. However, the amount of composition required is at least 750 ppm of which at least 450 ppm should be o-phenylphenol. This composition constitutes a certain improvement. However, in order to obtain satisfactory biocidal efficacy relatively high levels of the compositions are required.

It has now been found that when one utilises a biocidal composition comprising a mixture of o-phenylphenol and dichlorophene, the desired biocidal effect is achieved with a composition comprising lower levels of each of the effective compounds, i.e. a synergistic effect is observed. As will be shown hereinafter this synergistic effect is especially strong under actual field conditions, i.e. in the presence of organic soil.

The present invention thus consists in a biocidal composition comprising as active components a mixture of o-phenylphenol and 2,2'-methylene bis(4-chlorophenol) (dichlorophene).

In a preferred embodiment of the invention, said composition also comprises a surface active compound which is stable under basic conditions, for example, certain anionic surface active compounds, e.g. aliphatic sulfonates, sulfonates of aliphatic-aromatic hydrocarbons, ester sulfonates, amide sulfonates, and sulfonates containing ether, amino, keto and sulfone groups, as well as those obtained from sulfated fatty alcohols, sulfated fatty condensation products such as sulfated ethoxylated primary or secondary alcohols, and sulfated fatty glycerides, acids, esters, phosphates, and modified carboxylates, and mixtures thereof.

The composition according to the present invention is preferably applied in the form of the aqueous solution. The active compounds which as such are sparingly soluble in water are for this purpose utilized in the form of their sodium salts. Said sodium salts may be used as such or prepared in situ.

In order to save transport costs the composition is either sold in dry form or as a relatively concentrated aqueous solution. The amount of active components in the concentrated solution is preferably 30–50% and the amount of the surfactant, if present, is preferably 1.5–3.5%, all percentages being percentages by weight. Said solution can be diluted to the recommended use concentration, i.e. about 2-3 ml/L water. As will be shown hereinafter total concentrations of 500 ppm i.e. of 250 ppm of o-phenyl-phenol or even less, are very effective. This certainly constitutes a considerable advantage in comparison to the known compositions, which require higher levels.

The ratio of o-phenylphenol:dichlorophene may vary to a large extent. However, it appears that the most effective ratio is between 2:1 to 1:3.

The biocidal composition according to the present invention is not only effective against Pseudomonas but also against many other bacteria, such as Staphylocci, Streptococci, Brucella, Enterobacter, E. Coli, Proteus, Shigella and Salmonella. Moreover, it is effective against viruses in particular byophilic viruses such as:—

Newcastle Disease—Acute Asian type as in Israel—(-Velogenic Visceral Newcastle Disease);

Herpes simplex—Mareks Disease in Poultry;

Infectious Bronchitis;

Infectious Laryngotracheitis;

Influenza A2 Virus;

Adenovirus;

Vaccinia—Virus Causing Fox

The composition according to the present invention is also a broad spectrum fugicide. It kills algae, yeast, fungi and moulds. It prevents slime formation.

The composition according to the present invention is stable in the presence of organic matter. It retains its activity even in exaggeratedly hard water (over 700 ppm $CaCO_3$). It has a low toxicity.

In view of the above it is readily understood that the biocidal composition according to the present invention can be widely used in farm, home, hospital and industry. The low concentration of active components required and the high degree of efficacy makes the use very economical and safe.

The composition according to the present invention is prepared by methods known per se, i.e., by conventional mixing and dissolving operations.

The present invention will now be illustrated by the following examples without being limited by them.

In said examples the following solutions were utilized: a. 40% aqueous solution of dichlorophene and 2.1% of sodium lauryl ether sulfate. b. 40% aqueous solution of o-phenylphenol and 2.1% of sodium lauryl ether sulfate. Said solutions were mixed and/or diluted as required.

Wherever in the Examples a "composition" is stated this means a composition according to the present invention, i.e. a mixture of o-phenylphenol and dichloropheene. As in the case of a. and b. the composition also include the surfactant.

As Pseudomonas species there are utilised human, chicken and cattle strains of Pseudomonas aerogunosa. Said strains were isolated gt the Kimron Veterinary Institute from clinical outbreaks.

The microbioligical results were obtained as per the following procedure:

Bacterial dilutions of a fresh culture of the appropriate strain were incubated for 18 hours at 37° C. 0.2 ml of the bacterial culture at a concentration of $1 \times 10^7$ were then introduced into 1.8 ml of the appropriate dilution of the biocide. There was thus obtained a final bacterial concentration of $1 \times 10^6$.

After the stated contact time of the bacteria with the biocidal solution 0.1 ml of the solution was removed and introduced into 9.9 ml of physiological solution in order to neutralize the activity of the biocide.

Two samples were taken from said solution and each introduced into a nutrient broth (pH 7.2). A third sample was taken and introduced into a test-tube containing physiological solution. From the latter test-tube containing the physiological solution a sample was taken and added to a nutrient broth (pH 7.2).

The test tubes with the broth were then incubated for 18 hours at 37° C. and the presence of bacteria was checked and determined.

EXAMPLE 1

The efficacy of various concentrations of o-phenylphenol, dichlorophene and of the composition was tested against various strains (as indicated in the Tables) of Pseuodomonas aerogunosa for different contact times. This test was performed in clean solutions, i.e. no soil was added. The results are presented in the Tables I–III. The initial concentration of the bacteria in all experiments in all Examples was $1 \times 10^6$. The concentration of the biocide is given in ppm (parts per million) and the contact time in minutes. The results are indicated as follows:

+ = antibacterial efficacy (decrease of less than 210 g)
± = decrease of 2–4 log of the initial concentration of the bacteria = 99%–99.99% kill
− = kill (decrease of 4 log or more of the initial concentration of the bacteria = at least 99.99%)

a = Efficacy of dichlorophene

TABLE I

| Concentration | 4000 | | | 2000 | | | 1000 | | | 500 | | | 250 | | | 100 | | |
|---|---|---|---|---|---|---|---|---|---|---|---|---|---|---|---|---|---|---|
| Contact time | 2 | 5 | 10 | 2 | 5 | 10 | 2 | 5 | 10 | 2 | 5 | 10 | 2 | 5 | 10 | 2 | 5 | 10 |
| Human Strain | − | − | − | − | − | − | ± | − | − | ± | ± | − | + | + | ± | + | + | ± |
| Chicken Strain | − | − | − | − | − | − | − | − | − | + | − | − | + | ± | − | + | + | + |
| Cattle Strain | − | − | − | − | − | − | ± | − | − | + | ± | − | + | ± | − | + | + | + | b. Efficacy of o-phenylphenol

TABLE II

| CONCENTRATION | 4000 | | | 2000 | | | 1000 | | | 500 | | | 250 | | | 100 | | |
|---|---|---|---|---|---|---|---|---|---|---|---|---|---|---|---|---|---|---|
| Contact time | 2 | 5 | 10 | 2 | 5 | 10 | 2 | 5 | 10 | 2 | 5 | 10 | 2 | 5 | 10 | 2 | 5 | 10 |
| Human Strain | − | − | − | − | − | − | − | − | − | + | − | − | + | + | + | + | + | + |
| Chicken Strain | − | − | − | − | − | − | − | − | − | − | − | − | + | + | ± | + | + | + |
| Cattle Strain | − | − | − | − | − | − | − | − | − | ± | − | − | ± | ± | − | + | + | + |

Said test shows that a concentration of at least 500 ppm of o-phenylphenol is required.

c. Efficacy of composition (against chicken strain only)

TABLE III

| Concentration | 800 | | | 400 | | | 200 | | | 100 | | | 50 | | | 25 | | |
|---|---|---|---|---|---|---|---|---|---|---|---|---|---|---|---|---|---|---|
| Contact time | 2 | 5 | 10 | 2 | 5 | 10 | 2 | 5 | 10 | 2 | 5 | 10 | 2 | 5 | 10 | 2 | 5 | 10 |
| ratio o-phenylphenol dichlorophenone: | | | | | | | | | | | | | | | | | | |
| 1:1 | − | − | − | ± | − | − | ± | ± | − | + | + | + | | | | | | |
| 1:2 | − | − | − | ± | − | − | ± | − | − | ± | − | − | ± | ± | − | + | + | ± |
| 1:3 | − | − | − | − | − | − | + | − | − | + | − | − | + | ± | − | + | + | + |
| 2:1 | − | − | − | + | − | − | + | − | − | + | − | − | + | ± | ± | | | |

Said test shows that a concentration of both compounds totalling 400 ppm is sufficient, for contact times of 5 and 10 minutes, which demonstrates a synergistic effect.

EXAMPLE 2

The efficacy of dichlorophene and of o-phenylphenol was compared with that of various compositions for the chicken strain in the presence of 5% milk. The results are shown in Table IV.

TABLE IV

| Concentration | 4000 | | | 2000 | | | 1000 | | | 500 | | | 250 | | |
|---|---|---|---|---|---|---|---|---|---|---|---|---|---|---|---|
| Contact time | 2 | 5 | 10 | 2 | 5 | 10 | 2 | 5 | 10 | 2 | 5 | 10 | 2 | 5 | 10 |
| Dichlorophene | + | − | − | + | − | − | + | + | + | + | + | + | + | + | + |
| o-phenylphenol | − | − | − | − | − | − | − | − | − | + | − | − | + | + | + |
| ratio:o-phenylphenol:dichlorophene | | | | | | | | | | | | | | | | |
| 1:1 | − | − | − | − | − | − | − | − | − | − | − | − | − | − | − |
| 1:3 | − | − | − | ± | − | − | + | + | + | + | + | + | + | + | + |
| 2:1 | − | − | − | − | − | − | ± | − | − | ± | − | − | + | + | + |

Said test shows that under these conditions:
a. dichlorophene alone is effective only with concentrations of at least 2000 ppm
b. o-phenylphenol alone is effective only with concentrations of at least 500 ppm for contact times of 5 and 10 minutes c. the composition of the present invention of o-phenylphenol plus dichlorophene is effective at a total concentration of at least 500 ppm (ratios 1:1 and 2:1) which proves a synergistic effect.

EXAMPLE 3

The efficacy of dichlorophene and of o-phenylphenol was compared with that of various compositions for the chicken strain in the presence of 5% chicken manure. The results are shown in Table V.

TABLE V

| Concentration | 4000 | | | 2000 | | | 1000 | | | 500 | | | 250 | | |
|---|---|---|---|---|---|---|---|---|---|---|---|---|---|---|---|
| Contact time | 2 | 5 | 10 | 2 | 5 | 10 | 2 | 5 | 10 | 2 | 5 | 10 | 2 | 5 | 10 |
| Dichlorophene | − | − | − | ± | − | − | + | − | − | + | ± | − | + | + | + |
| o-phenylphenol | − | − | − | − | − | − | + | − | − | + | − | − | + | ± | ± |
| ratio-o-phenyl-phenol:dichlorophene | | | | | | | | | | | | | | | |
| 1:1 | − | − | − | − | − | − | − | − | − | − | − | − | + | ± | + |
| 1:3 | − | − | − | − | − | − | ± | − | − | + | ± | − | + | + | + |

Said tests demonstrate that under these conditions:
a. dichlorophene alone is effective only with concentrations of at least 1000 ppm with contact times of 5 and 10 minutes
b. o-phenylphenol of the present invention is effective with concentrations of at least 500 ppm with contact times of 5 and 10 minutes
c. the composition is effective even at a contact time of 2 minutes with a total concentration of 500 ppm (1:1).

These results demonstrate that a prompt and synergistic efficacy of said composition is achieved.

EXAMPLE 4

The efficacy of dichlorophene and of o-phenylphenol was compared with that of various compositions against E. Coli O$_{111}$B$_4$. The tests were performed as follows:

The disinfectants were diluted with deionized water to the desired concentrations.

0.2 cc of a fresh 18 hour culture containing approximately 10$^8$ org/ml was added to 1.8 cc of the diluted disinfectant. After exactly 5 minutes reaction time and again after exactly 5 additional minutes, 0.1 cc was transferred to a tube containing 9.9 cc sterile deionized water and mixed well. 0.1 cc of this was then plated on Mueller Hinton Agar in a disposable petri dish, and spread evenly over the entire surface using a glass spreader. The plates were then incubated for 24 hours at 35° C. and the number of surviving colonies counted.

The results are shown in Table VI.

TABLE VI

| Concentration in p.p.m. | No. of surviving colonies/treatment time | | | | | |
|---|---|---|---|---|---|---|
| | Dichlorophene | | Mixture 1:1 | | O-phenyl phenol | |
| | 5' | 10' | 5' | 10' | 5' | 10' |
| 2000 | 0 | 0 | 0 | 0 | 0 | 0 |
| 1000 | 0 | 0 | 0 | 0 | 80 | 0 |
| 500 | 600 | 0 | 0 | 0 | 600 | 12 |
| 250 | 1500 | 300 | 0 | 0 | no inhib. | no inhib. |
| 125 | no inhib. | 300 | 360 | 0 | no inhib. | no inhib. |
| 62.5 | no inhib. | 1500 | 800 | 480 | no inhib. | no inhib. |

Said tests demonstrate that under these conditions
a. dichlorophene alone is effective only with concentrations of at least 250 ppm with contact times of 5 and 10 minutes.
b. o-phenyl phenol alone is effective only with concentrations of at least 500 ppm with contact times of 5 and 10 minutes.
c. the composition in a ratio 1:1 is effective in concentrations as low as 62.5 ppm at contact times of 5 and 10 minutes.

These results demonstrate that a prompt and synergistic efficacy of said composition is achieved.

I claim:

1. A bactericidal composition comprising as essential coactive ingredients o-phenylphenol and 2,2'-methylene bis (4-chlorophenol) in a ratio of 1:1.

2. Liquid bactericidal composition comprising an aqueous solution of the composition of claim 1.

3. Liquid bactericidal composition according to claim 2 wherein said coactive ingredients are present in an amount of 30–50% by weight.

4. Liquid bactericidal composition according to claim 2 and also including 1.5–3% by weight of a surface active agent.

5. Liquid bactericidal composition according to claim 2 wherein said coactive ingredients are present in an amount of 400–750 ppm.